(12) United States Patent
Russell

(10) Patent No.: US 7,263,159 B2
(45) Date of Patent: *Aug. 28, 2007

(54) INTERMEDIATE DENSITY MARKER AND A METHOD USING SUCH A MARKER FOR RADIOGRAPHIC EXAMINATION

(75) Inventor: Donald G. Russell, Kensington, CT (US)

(73) Assignee: Beekley Corporation, Bristol, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/285,572

(22) Filed: Nov. 21, 2005

(65) Prior Publication Data

US 2006/0072706 A1   Apr. 6, 2006

Related U.S. Application Data

(63) Continuation of application No. 09/372,835, filed on Aug. 12, 1999, now Pat. No. 6,985,558, which is a continuation of application No. 08/934,121, filed on Sep. 19, 1997, now Pat. No. 6,041,094, which is a continuation of application No. 08/372,658, filed on Jan. 13, 1995, now abandoned, which is a continuation-in-part of application No. 08/059,201, filed on May 7, 1993, now Pat. No. 5,383,233.

(51) Int. Cl.
*A61B 6/04* (2006.01)

(52) U.S. Cl. ....................................................... 378/37

(58) Field of Classification Search ............... 378/20, 378/37, 162, 163, 205, 207; 600/426
See application file for complete search history.

(56) References Cited

U.S. PATENT DOCUMENTS

| | | | |
|---|---|---|---|
| 1,168,177 A | 1/1916 | De Yoanna | |
| 1,912,464 A | 6/1933 | Powers | |
| 2,120,064 A | 6/1938 | Buckley | |
| 2,126,608 A | 8/1938 | Brady | |
| 2,141,193 A | 12/1938 | Mott | |

(Continued)

FOREIGN PATENT DOCUMENTS

DE   3015779 A1   10/1981

(Continued)

OTHER PUBLICATIONS

"Bethea-Goodman Marker", X-Ray Supplies, GE X-Ray Corporation, p. 13, 1932.

(Continued)

*Primary Examiner*—Edward J. Glick
*Assistant Examiner*—Anastasia S. Midkiff
(74) *Attorney, Agent, or Firm*—McCarter & English, LLP

(57) ABSTRACT

The present invention provides a partially radiolucent, partially radiopaque marker and a method for using such a marker for radiographic examination. The marker and the disclosed method may be employed for the examination of tissue structures of various densities. The radiographic density and thickness of the marker are selected so that when the marker and an underlying tissue structure are exposed to x-ray radiation of a specified energy, the marker casts a legible shadow without obscuring anatomical detail present in the underlying tissue structure. The invention also provides a system of partially radiolucent, partially radiopaque markers for use in the method of radiographic examination taught by the invention.

26 Claims, 6 Drawing Sheets

U.S. PATENT DOCUMENTS

| | | |
|---|---|---|
| 2,162,420 A | 6/1939 | Buckley |
| 2,255,099 A | 9/1941 | Brady |
| 2,329,187 A | 9/1943 | De Lorimier et al. |
| 2,387,704 A | 10/1945 | McLachlan, Jr. |
| 2,417,497 A | 3/1947 | Hulslander, Sr. |
| 2,912,140 A | 11/1959 | Cole |
| 2,939,958 A | 6/1960 | Andersson |
| 2,943,628 A | 7/1960 | Howell |
| 2,972,350 A | 2/1961 | Deker |
| 3,097,636 A | 7/1963 | Haynes, Jr. et al. |
| 3,155,091 A | 11/1964 | Nissenbaum et al. |
| 3,217,705 A | 11/1965 | Billings |
| 3,267,623 A | 8/1966 | Block |
| 3,270,122 A | 8/1966 | Biken |
| 3,302,634 A | 2/1967 | Mazellan |
| 3,302,637 A | 2/1967 | Mazellan |
| 3,464,415 A | 9/1969 | Brownlee |
| 3,547,121 A | 12/1970 | Cherry |
| 3,836,776 A | 9/1974 | Gullekson |
| 3,848,136 A | 11/1974 | Seldin |
| 3,917,952 A | 11/1975 | Jackson |
| 3,941,127 A | 3/1976 | Froning |
| 3,952,194 A | 4/1976 | Bayonnett |
| 3,965,907 A | 6/1976 | Hardy et al. |
| 3,972,350 A | 8/1976 | Pickett |
| 4,027,659 A | 6/1977 | Slingluff |
| 4,029,285 A | 6/1977 | Tendler |
| 4,048,507 A | 9/1977 | De Gaston |
| 4,102,331 A | 7/1978 | Grayzel et al. |
| 4,259,585 A | 3/1981 | Novak et al. |
| 4,319,136 A | 3/1982 | Jinkins |
| 4,328,814 A | 5/1982 | Arkans |
| 4,339,035 A | 7/1982 | Marcus et al. |
| 4,442,315 A | 4/1984 | Segawa |
| 4,460,804 A | 7/1984 | Svejkovsky |
| 4,506,676 A | 3/1985 | Duska |
| 4,529,635 A | 7/1985 | Sheldon |
| 4,543,958 A | 10/1985 | Cartmell |
| 4,563,768 A | 1/1986 | Read et al. |
| 4,589,406 A | 5/1986 | Florek |
| 4,691,333 A | 9/1987 | Gabriele et al. |
| 4,764,948 A | 8/1988 | Hurwitz |
| 4,798,212 A | 1/1989 | Arana |
| 4,813,062 A | 3/1989 | Gilpatrick |
| 4,838,265 A | 6/1989 | Cosman et al. |
| 4,838,273 A | 6/1989 | Cartmell |
| 4,846,681 A | 7/1989 | Mourany et al. |
| 4,854,323 A | 8/1989 | Rubin |
| 4,860,331 A | 8/1989 | Williams et al. |
| 4,875,478 A | 10/1989 | Chen |
| 4,911,169 A | 3/1990 | Ferrari |
| 4,916,170 A | 4/1990 | Nambu et al. |
| 4,918,715 A | 4/1990 | Krupnick et al. |
| 4,922,924 A | 5/1990 | Gambale et al. |
| 4,941,164 A | 7/1990 | Schuller et al. |
| 4,953,193 A | 8/1990 | Robinson |
| 4,985,019 A | 1/1991 | Michelson |
| 5,052,035 A | 9/1991 | Krupnick |
| 5,086,445 A | 2/1992 | Fisher et al. |
| 5,095,499 A | 3/1992 | Wentz |
| 5,191,886 A | 3/1993 | Paeth et al. |
| 5,193,106 A | 3/1993 | Desena |
| 5,247,555 A | 9/1993 | Moore et al. |
| 5,275,622 A | 1/1994 | Lazarus et al. |
| 5,282,254 A | 1/1994 | Chiu et al. |
| 5,368,030 A | 11/1994 | Zinreich et al. |
| 5,394,456 A | 2/1995 | Livingston |
| 5,427,099 A | 6/1995 | Adams |
| 5,469,847 A | 11/1995 | Zinreich et al. |
| 5,493,601 A | 2/1996 | Fivez et al. |
| 5,602,895 A | 2/1997 | Fivez et al. |
| 5,702,128 A | 12/1997 | Maxim et al. |
| 6,041,094 A * | 3/2000 | Russell ........................ 378/37 |
| 6,985,558 B1 * | 1/2006 | Russell ........................ 378/162 |

FOREIGN PATENT DOCUMENTS

| | | |
|---|---|---|
| EP | 0387103 A1 | 9/1990 |
| FR | 2166671 | 8/1973 |
| GB | 1458196 | 12/1976 |
| JP | 5-68678 | 5/1993 |

OTHER PUBLICATIONS

"X-Rite Radio Opaque Label Tape", X-Ray Identification Corporation, 1965.

"Preoperative Localization", Radiology 146: 833-835 , Mar. 1983.

E. Mark Levinsohn, MD "Device for Facilitating Lesion Localization", Radiology 1991.

"Facial Fractures", RadioGraphics, vol. 4, No. 4, Jul. 1984.

Mark J. Homer, MD-Eliza R. Pile-Spellman, MD "Needle Localization" Radiology 1986.

Peter R. Mueller, MD et al "Obstruction of the Left Hepatic Duct", Radiology Nov. 1982.

Terrence M. Peters, Peters, Ph.D et al "Integrated Stereotaxic Imaging with CT", Radiology 1986.

James T. Dobbins III, Ph.D "Threshold Perception Performance with Computed and Screen-Film Radiography" Radiology 1992.

Leo . Schultz Kool, MD et al "Advanced Multiple-Beam Equalization Radiography in Chest Radiology" *Radiology* 1988.

Jingsxi Zhang, Ph.D et al "Multimodality Imaging of Brain Structures for Stereotactic Surgery", *Radiology* 1990.

Kyo Rak Lee, MD et al "State-of-the-Art Digital Radiography" *RadioGraphics* 1991.

Carol J. Mount, RTR, Joel E. Gray, Ph.D "Improved Tool for Testing Screen-Film Contact in Mammography" *RadioGraphics* 1990.

Daniel B. Kopans, MD, Jack E. Meyer, MD *Radiology*, Oct. 1982.

Arnold Herskovic, MD et al "Utilization of the Computed Tomography Scanner in Interstitial Dosimetry" *Radiology*, Jun. 1980.

Rauf Yagan "Mammographic Needle Localization of Lesions Seen in Only One View" *Radiology*, Jan. 7, 1995.

Wing-Chee Lam, Ph.D et al "On-line Portal Imaging: Computer-assisted Error Measurement" *Radiology*, 1991.

Patricia M. Johnson, D.Sc. et al "A Double-Junction Technique for Total Central Nervous System Irradiation with a 4-MV Accelerator" *Radiology*, Nov. 1982.

Young H. Kim, MD et al "Radiation Tolerance of the Cervical Spinal Cord" *Radiology*, May 1981.

Cornelia M. Schaefer, MD et al "Improved Control of Image Optical Density with Low-Dose Digital and Conventional Radiography in Bedside Imaging" *Radiology* 1989.

Seungho H. Lee, MD et al "Localization of Vertex Lesions on Cranial Computed Tomography" *Radiology* Feb. 1980.

Aubrey M. Palestrant, MD "Comprehensive Approach to CT-guided Procedures with a Hand -held Guidance Device" *Radiology* 1990.

H. Joachim Burhenne, MD et al "Silicone Drain Mimicking a Surgical Sponge" *Radiology* 1982.

Heber MacMahon, MD et al "Laser Alignment System for High-Quality Portable Radiography" *RadioGraphics* 1992.

Clyde A. Helms, MD et al "Detection of done-marrow Metastases Using Quantitative Computed Tomography" *Radiology* Sep. 1981.

David W. Nelson, MD et al "CT-guided Fixation of Sacral Fractures and Sacroiliac Joint Disruptions" *Radiology* 1991.

Jay S. Cooper, MD et al "Afterloading Mold Therapy: A New Look at a Time Honored Concept" *Radiology* May 1980.

John H. Mayer, MD et al "A Localization Grid for Percutaneous Transluminal Angioplasty" *Radiology* Aug. 1982.

Brian S. Garra, MD et al "Visibility of Gallstone Fragments at US and Fluoroscopy: Implications for Monitoring Gallstone Lithotripsy" *Radiology* 1990.

E. Meredith James, MD et al "High-Resolution Dynamic Ultrasound Imaging of the Carotid Bifurcation: A Prospective Evaluation" *Radiology* Sep. 1982.

David R. Haynor, MD, Ph.D et al "Radiotherapy Planning: Direct Tumor Location of Simulation and Port Films Using CT" *Radiology* 1986.

Douglas C. Smith, MD et al "Medial Brachial Fascial Compartment Syndrome: Anatomic Basis of Neuropathy after Transaxillary Arteriography" *Radiology* 1989.

Paul C. Hajek, MD et al "Localization Grid for MR-guided Biopsy" *Radiology* 1987.

Kenneth A. Bell, MD "Vidiofluoroscopy During Arthrography of the Temporomandibular Joint" *Radiology*, Jun. 1983.

Gerald Cohen, Ph.D. et al "Evaluation of a Digital Subtraction Angiography Unit" *Radiology*, Aug. 1982.

Robert S. Wenstrup, Ph.D. et al Digital Subtraction Angiography System Evaluation with Phantoms *Radiology*, 1985.

Michael J. Landay, MD et al "Apparatus Seen on Chest Radiographs after Cardiac Surgery in Adults" *Radiology*, 1990.

Barbara A. Carroll, MD "US of the Gastrointestinal Tract" *Radiology* 1989.

Frans G. Scholten, MD et al "US Location of the Adductor Canal Hiatus: Morphologic Study" *Radiology* 1989.

Barbara J. Weinstein, MD et al "Ultrasonography of Pancreatic Lithiasis" *Radiology* Jan. 1880.

Yasuyuki Akine, MD et al Clinical Merit of Simulation Images Generated From CT *Radiology* Nov. 1982.

H.J. Gent, MD et al Stereotaxic Needle Localization and Cytological Diagnosis of Occult Breast Lesions Mar. 24, 1986.

Harry H. Chen, MD et al "Needle Localization of Nonpalpable Breast Lesions with a Portable Dual-Grid Compression System" *Radiology* 1989.

Daniel B. Kopans, MD et al Spring hookwire Breast Lesion Localizer: Use with Rigid-compression Mammographic Systems *Radiology* 1985.

Jeffrey S. Ross, MD "Thoracic Disk Herniation: MR Imaging" *Radiology* Jun. 1988.

James H. Watt, MD "Double Cortical Line in the Acetabular Roof: A Sign of Disuse Osteoporosis" *Radiology* vol. 167, No. 3 (Undated).

Donald J. Widder, MD "Localization Grid for MR-guided Biopsy" *Radiology* vol. 166, No. 2 (Undated).

Rauf Yagan et al "Mammographic Needle Localization of Lesions Seen in Only One View" *AJR* May 1985.

"Bethea-Goodman Marker", X-Ray Supplies, GE X-Ray Corporation, p. 13, 1932.

"X-Rite Radio Opaque Label Tape", X-Ray Identification Corporation, 1965.

\* cited by examiner

INTERMEDIATE DENSITY MARKER AND A METHOD USING SUCH A MARKER FOR RADIOGRAPHIC EXAMINATION

CROSS-REFERENCE TO RELATED APPLICATIONS

This application is a continuation of application Ser. No. 09/372,835 filed Aug. 12, 1999, now U.S. Pat. No. 6,985,558 which is a continuation of application Ser. No. 08/934,121 filed Sep. 19, 1997, now U.S. Pat. No. 6,041,094, which is a continuation of application Ser. No. 08/372,658, filed Jan. 13, 1995, now abandoned, which is a continuation-in-part of application Ser. No. 08/059,201, filed May 7, 1993, now U.S. Pat. No. 5,383,233, which is a continuation-in-part of the co-pending application Ser. No. 09/372,835, filed Aug. 12, 1999, all of which are expressly herein incorporated by reference as part of the present disclosure.

BACKGROUND OF THE INVENTION

This present invention relates generally to the field of a radiography and, more particularly, to a marker of intermediate density and a method of radiographic examination using such a marker. The invention further relates to a system of radiographic markers for use in such a method.

To convey pertinent information on radiographic film, radiologists and technicians frequently use markers which absorb x-rays and cast a shadow when placed within the x-ray exposure field. Such markers are positioned either directly on a patient undergoing radiographic examination or on the cassette holding the radiographic film.

For example, right and left markers are routinely used to designate the anatomical orientation of the patient or to identify a particular extremity being examined. Markers are also used in trauma cases to localize the trauma site by placing the marker on the skin surface at the appropriate location prior to x-ray exposure. Further, markers are often placed on the surface of the examination table or the film cassette, within the exposure field but outside the image of the patient, to define the patient's physical orientation in relationship to the x-ray beam or the film, i.e., erect, prone, supine or decubitus.

In the past, radiographic markers have been constructed of materials having a high atomic number such as, for example, lead, mercury, steel or heavy metal salts. When exposed to x-rays, markers having such high density completely attenuate the x-ray beam and cast a distinct shadow that is readily apparent on the x-ray film. The disadvantage here is that any tissue detail that falls within the shadow of the marker will be completely obscured. Metallic markers also create problems when employed in computerized tomography (CT) applications. CT scanners, which typically operate in the range of 60 to 80 KV, cannot tolerate the presence of metallic objects in the radiographic field. Such dense objects cause streaking which degrades the radiographic image. This problem is made more acute by the fact that the marker must have sufficient surface area to be imaged in at least one section radio graphed by the scanner. A metallic marker having the required surface area would completely disrupt the scanning apparatus.

Accordingly, it has been the practice of those skilled in the art of general radiography to place such markers on the patient or the radiographic film outside the area of clinical concern. This practice encourages increasing the size of the x-ray field to ensure that the image of an important marker appears on the film. Unfortunately, one result of such a practice is that the patient's body is exposed to potentially harmful radiation beyond the specific site being examined. In cases where a radiographic examination is conducted and the image of a marker is not clearly visible within the exposure field, the exam is often repeated to either enlarge the exposure field or to reposition the marker. Again, the unfortunate result is that the patient is exposed to greater dosage of potentially harmful radiation.

To precisely locate a tissue area of particular concern on the radiographic film following exposure, there are circumstances where a marker is placed on a patient and purposely imaged while overlying anatomical structures. In such a case, it is the usual practice of those skilled in the art to use a small, metal, spherical marker measuring no more than about 1 to 2 mm in diameter. While the shadow from such a small marker is less likely to obscure important tissue detail, the shadow may be mistaken for a physiological calcification or an opaque foreign body. Further, because such a marker is necessarily of small size with a correspondingly small shadow, there is an inherent difficulty in discerning variations in the size and shape of the marker's image on the film. Thus, the information that can be conveyed by markers of this type is limited.

Finally, markers comprising lead, mercury and other toxic heavy metals cannot be deposited in landfills or incinerated and thus present a potential environmental hazard if improperly disposed of. This problem is exacerbated by the fact that during radiographic examination procedures markers are often contaminated by body fluids. While contaminated markers can be sterilized, to save time and expense they are, more typically, discarded after only a single use.

It is therefore an object of the invention to provide a radiographic marker which may be placed on a tissue structure and imaged without obscuring underlying anatomical detail.

It is a further object of the invention to provide such marker which is constructed from non-toxic material.

It is a still further object of the invention to provide markers of this type in various sizes and shapes to convey pertinent information on radiographic film.

It is another object of the invention to provide a marker for use in CT applications which may be placed on a tissue structure and imaged without obscuring underlying anatomical detail.

It is yet another object of the invention to provide a method of radiographic examination using such markers.

SUMMARY OF THE INVENTION

The present invention meets these and other objects by providing a partially radiolucent, partially radiopaque marker for the radiographic examination of underlying tissue structures. The marker has a radiographic density and thickness selected to permit the marker to both cast a radiographic shadow and transmit sufficient radiation to image anatomical detail present in the tissue structure when the marker and the tissue structure are exposed to an x-ray beam.

In a second aspect, the invention provides a method for radiographic examination which includes the steps of providing a source of x-ray radiation capable of generating an x-ray beam of sufficient energy to image a tissue structure exposed to the beam, and positioning the above-described intermediate density marker between the source of the x-ray radiation and the tissue structure. Once the marker has been properly positioned, the marker and the tissue structure are exposed to the x-ray beam to generate a radiographic image of the structure with the shadow of the marker superimposed thereon. Since the radiographic density and thickness of the marker have been carefully selected to meet the criteria set forth above, anatomical detail present in the tissue structure is clearly visible through the shadow cast by the marker.

In another aspect, the present invention provides a system of intermediate density markers for use in the radiographic examination of tissue structures representing a range of tissue densities. Tissues representing the range of densities for which the markers comprising the system may be used include, for example: breast tissue and other soft tissues having a density approximately equal to that of water; intermediate density tissues, such as the bones of the extremities; and very dense tissues such as the skull, spine and the tissues comprising the chest and other thick body parts.

Each of the markers comprising the system has a radiographic density and thickness which permit the marker, upon exposure of the marker and an underlying tissue structure to x-ray radiation of a specific energy, to both cast a radiographic shadow and transmit sufficient radiation to image anatomical detail present in the underlying tissue structure.

DETAILED DESCRIPTION OF THE INVENTION

Figure 1:
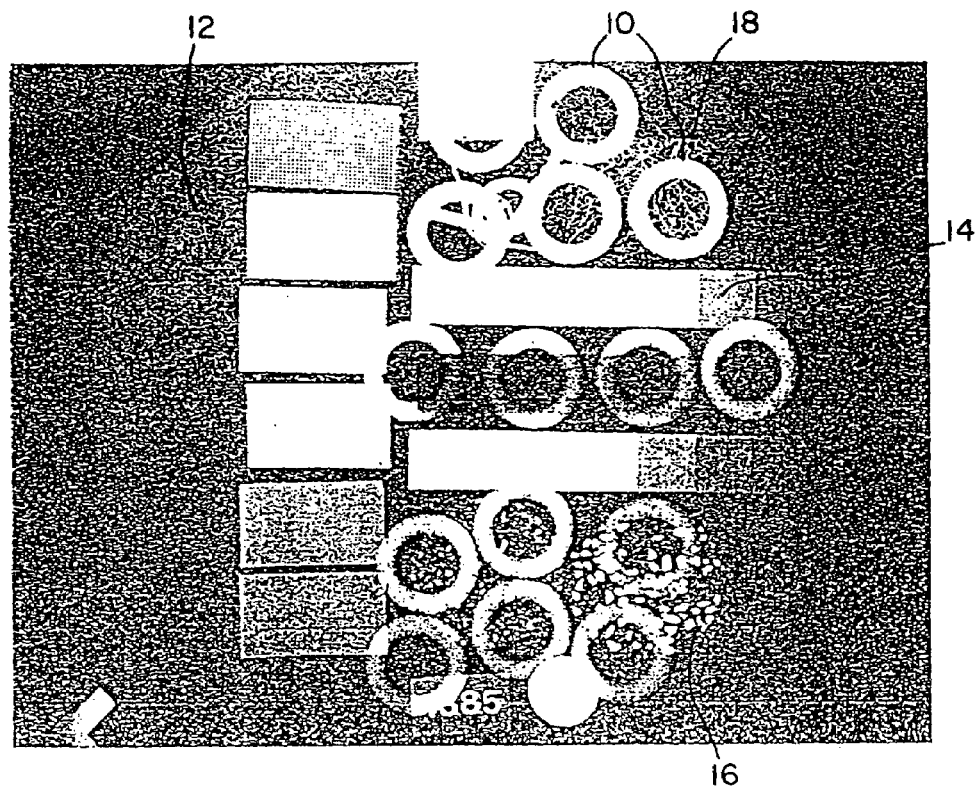
FIG. 1 is a radiograph of several rubber collars useful in practicing the method of the present invention imaged on the surface of a mammography phantom.

The most important factor regarding the detail recorded in a radiographic image is the disparity in light and dark or shadow intensity between adjacent objects. This is called image contrast and refers to the difference in the optical density between areas or objects imaged on a detectors, commonly photographic film. As x-rays pass through a patient, or other objects, they are absorbed, to varying degree, by the materials through which they pass. The principal determinant of contrast is the radiation attenuation property of each material, which is a function of the material's elemental and chemical composition. Materials of higher atomic number and density (weight per volume) have a greater ability to absorb x-rays and reduce or attenuate the beam.

In the diagnostic x-ray spectrum, for example, bone, rich in calcium, contrasts very well with the surrounding muscle and other soft tissues which have a density equivalent to water. Fatty tissue, which is only 10% less dense than muscle, is not clearly distinguished from other soft tissues because of the lack of a significant attenuation differential.

These same conditions hold for all chemical compounds and mixtures, biological and non-biological.

Image contrast, as recorded radiographically, may be expressed mathematically, for a given spectrum of x-rays, as follows:

$$C = (D2 - D1)/D1$$

Where C=the optical contrast differential between objects D1 and D2 as recorded on a radiograph.

Where D2=the attenuating ability of object D2.

Where D1=the attenuating ability of an adjacent object or the background attenuation.

If a thin, uniform, moderate attenuator is placed in the x-ray beam, the overall quantity of x-ray in its path is uniformly and moderately reduced. Applied to the contrast equation shown above, this additional uniform attenuation shows up as an equal quantity in the numerator and the denominator. Mathematically, then, these additional figures cancel out and, C, representing the contrast differential between D2 and D1 is unchanged.

Utilizing these principles, the present invention provides a partially radiolucent, partially radiopaque marker having a uniform density and thickness for use in radiographic examination. Depending on the density of the particular tissue structure being examined and the corresponding radiation energy required, the density and thickness of the marker are selected so that upon exposure of the marker and an underlying tissue structure to the radiation, the marker will cast a legible shadow on radiographic film without obscuring radiographic anatomical detail present in the underlying tissue structure.

With regard to the range of tissue densities presented in human diagnostic radiology and the corresponding radiation energies required, those skilled in the art are well aware that soft tissue, such as breast tissue and other tissues having a density approximately that of water, require the application of "soft" radiation, generally in the range of from about 20 KV to about 40 KV. More dense tissue, such as bone tissue in the extremities, requires radiation in the range of from 40 KV to about 70 KV. Finally, very dense tissue such as, for example, the skull, spine and the tissue structures comprising the chest, require more intense radiation in the range of from about 70 KV to about 120 KV.

Accordingly, the present invention encompasses markers of varying density and thickness which may be used for the radiographic examination of tissues representing the broad range of tissue densities noted above. In general, a marker is designed to absorb from about 2% to about 75% of the incident radiation. However, it must be appreciated that the invention is in no way limited in this regard and that the markers may absorb more or less radiation depending on the particular tissue being imaged and its density. The governing parameters are that the marker must exhibit sufficient radiolucency to provide a discernible image when exposed to radiation and at the same time exhibit sufficient radiopacity so as not to obscure the underlying tissue detail.

Thus, it is no longer necessary, as with prior art radiographic markers and methods of examination, to completely attenuate the x-ray beam to achieve a consistent and easily discernible image of the marker on the film. As explained more fully below in connection with the Figures, there is a broad range of materials of intermediate density which can be used to construct the markers taught by the invention.

Referring now to FIG. 1, a number of rubber O-shaped collars 10 having a thickness of from about 1.5 mm to about 2 mm are shown radiographed on the surface of a Kodak mammography phantom 12. The exposure is at 28 KV, and the collars are equivalent to about 1.2 mm of aluminum, as established by the aluminum step wedge 14, which is graduated in 0.2 mm increments. Markers of this type are useful in imaging soft tissue at a radiation energy ranging from about 20 KV to about 40 KV and are particularly useful in mammography. As FIG. 1 illustrates, the markers have sufficient radiopacity to cast a discernible image and are sufficiently radiolucent to permit the simulated micro calcifications 16 and fine tissue details 18 to be clearly imaged.

Figure 2:
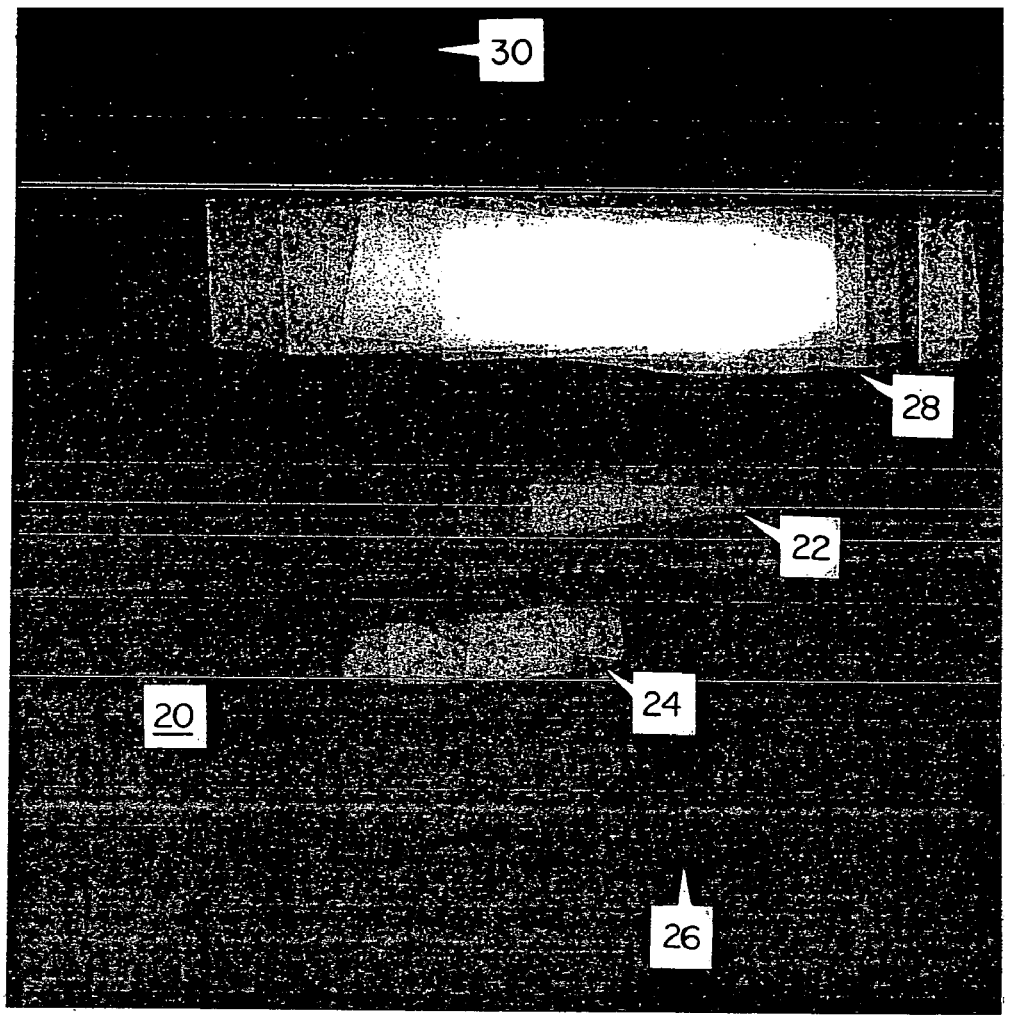
FIG. 2 is a radiograph of rubber, aluminum and vinyl markers useful in practicing the method of the present invention imaged on the surface of the American College of Radiology quality assurance phantom.

FIG. 2 illustrates additional examples of markers useful in radiographing low density tissue structures. The markers are constructed of rubber, aluminum and vinyl and are shown radiographed on the surface of the American College of Radiology quality assurance phantom ("ACR phantom 006 294"). The exposure is at 26 KV, and the radiograph was made using a photo-timed mammography machine available from General Electric. As is well-known to those skilled in the art, the ACR phantom 20 approximates breast tissue density and has simulated calcifications and nylon low density "nodules".

Markers 22 comprise strips of rubber having a thickness of about 0.2 inches and a density approximately equal to 0.115 inches of aluminum. Markers 24 also comprise strips of rubber, and the strips have a thickness of 0.1 inches. Markers 26 comprise plastic strips having a thickness of about 0.1 inches, and markers 28 are strips of aluminum having a thickness of 0.115 inches. Finally, markers 30 are strips of vinyl 0.1 inches thick.

As FIG. 2 illustrates, markers comprised of these various materials cast a legible shadow without obscuring underlying detail when exposed to radiation energies typically employed in radiographing low density soft tissue. Generally, rubber markers having a thickness of from about 0.2 inches to about 0.4 inches are appropriate for radiographing soft tissue. With respect to plastic and aluminum markers, thicknesses ranging from 0.1 inches to about 0.2 inches and from about 0.011 inches to about 0.022 inches, respectively, have been found useful. Vinyl markers provided in thicknesses ranging from about 0.75 mm to about 1 mm have been found useful.

Figure 3:
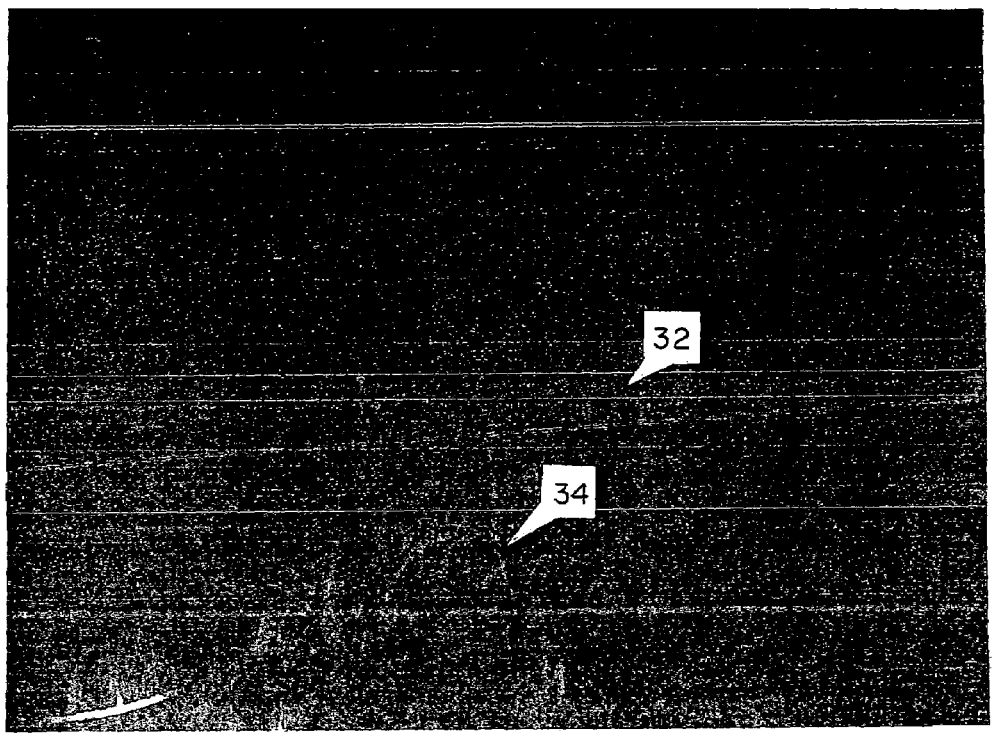
FIG. 3 is a cranio-caudal view of a patient's left breast with a vinyl marker useful in practicing the method of the invention positioned on the surface thereof.

The utility of markers constructed from vinyl for radiographing soft tissue structures without obscuring underlying detail is further illustrated in FIG. 3. FIG. 3 is a craniocaudal view of a patient's left breast 32 with a vinyl marker 34 positioned on the surface thereof to mark the location of scar tissue. As FIG. 3 illustrates, the anatomical detail in the breast tissue directly underlying the anterior marker 34 is clearly visible on the radiograph.

Figures 4A, 4B:
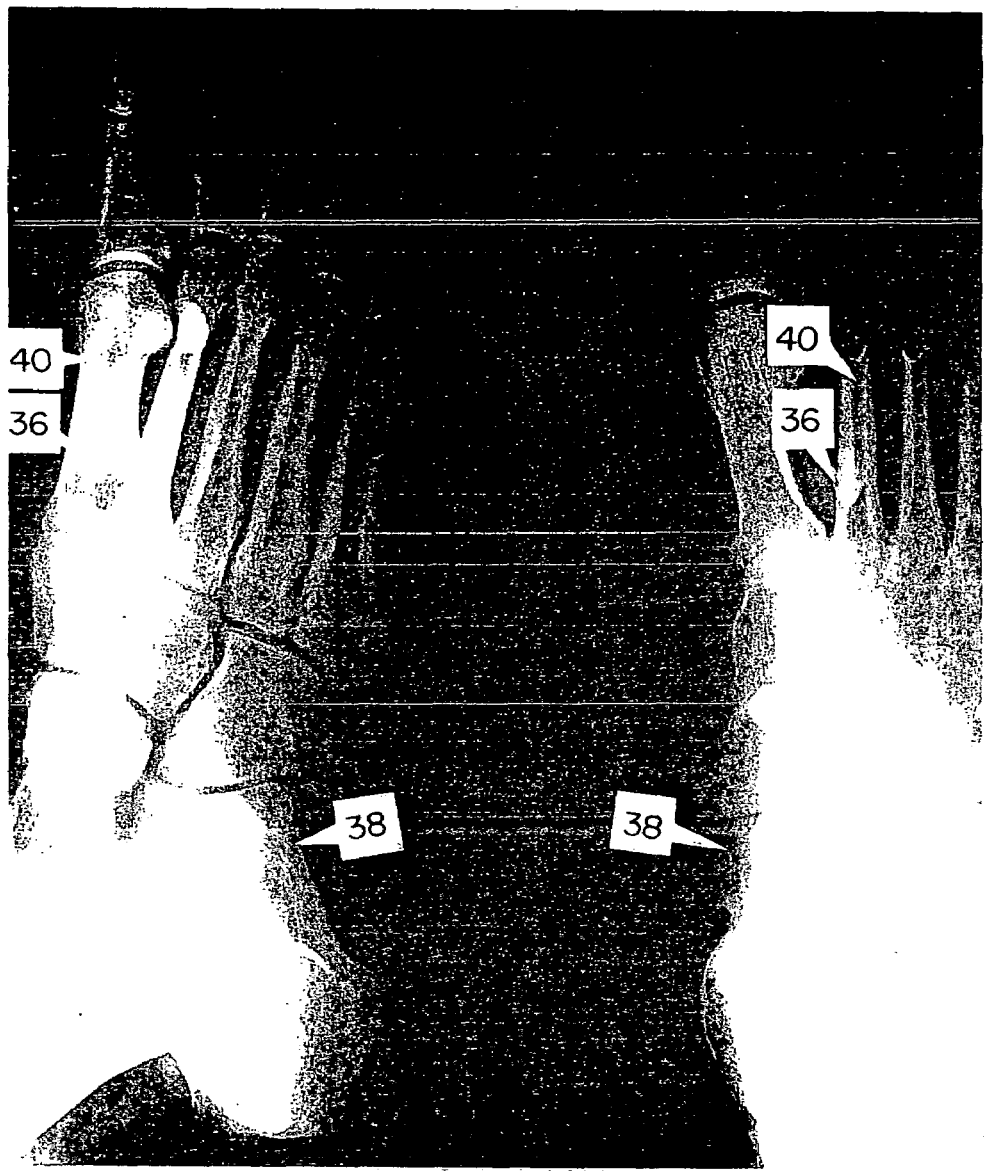
FIG. 4(a) is a posterior view of a plastic/barium sulfate marker useful in practicing the method of the present invention radio graphed on the surface of a patient's foot.
FIG. 4(b) is an oblique view of the marker shown in FIG. 4(a).

FIG. 4 illustrates posterior and oblique views of a plastic/barium sulfate marker useful for radiographing more dense tissues at energy levels from about 40 to about 70 KV. The marker 36 is plastic impregnated with 40% barium, and it is shown imaged on the surface of a patient's foot 38. Note that the anatomical detail in the bone 40 underlying the marker 36 is clearly visible.

Markers constructed of barium impregnated plastic have been found to be particularly useful in practicing the present invention because the density of the markers can be easily and precisely selected by varying the barium content of the plastic. Thus, an entire selection or system of barium impregnated plastic markers is provided for the entire range of tissue densities and exposure energies typically encountered by those skilled in the art.

Figure 5:
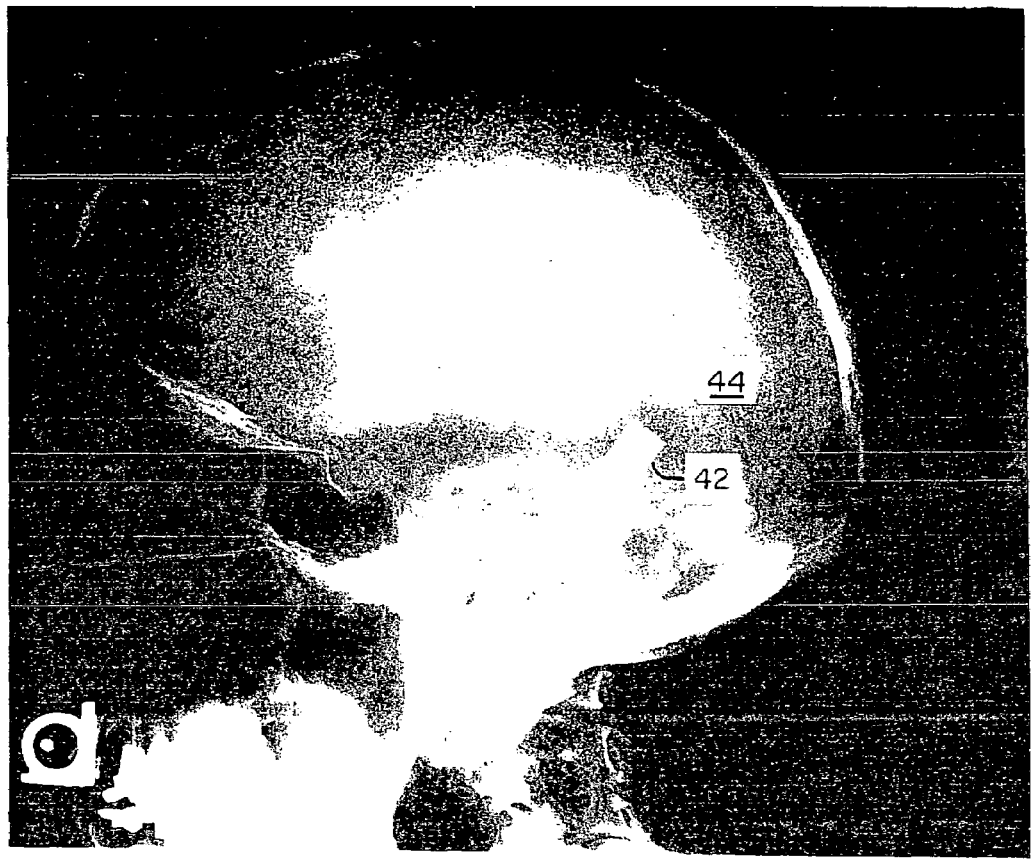
FIG. 5 is a radiograph of a plastic/barium sulfate marker useful in practicing the method of the present invention imaged on the surface of a patient's skull.

FIG. 5 shows a plastic/barium sulfate marker useful for radiographing very dense tissues, such as the bones of the skull, face and hip, at energy levels from about 70 to about 120 KV. The marker 42 is plastic impregnated with 40% barium and is cut from sheets measuring between 0.015-0.02 inches in thickness. The marker 42 is shown imaged on the surface of a patient's skull 44, and the radiograph shows that the marker images well at one to two layers of the sheet material (0.015-0.040 inches). The marker is most useful at a thickness of about 0.030-0.040 inches where it has sufficient density to be clearly visible on the radiograph, and yet permit sufficient penetration of the radiation to provide imaging of the diagnostic object contrast.

Figure 6:
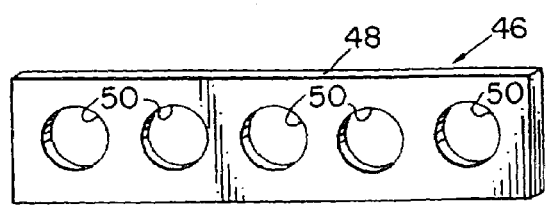
FIG. 6 is a perspective view of a marker useful for practicing the method of the invention.
Figure 7:
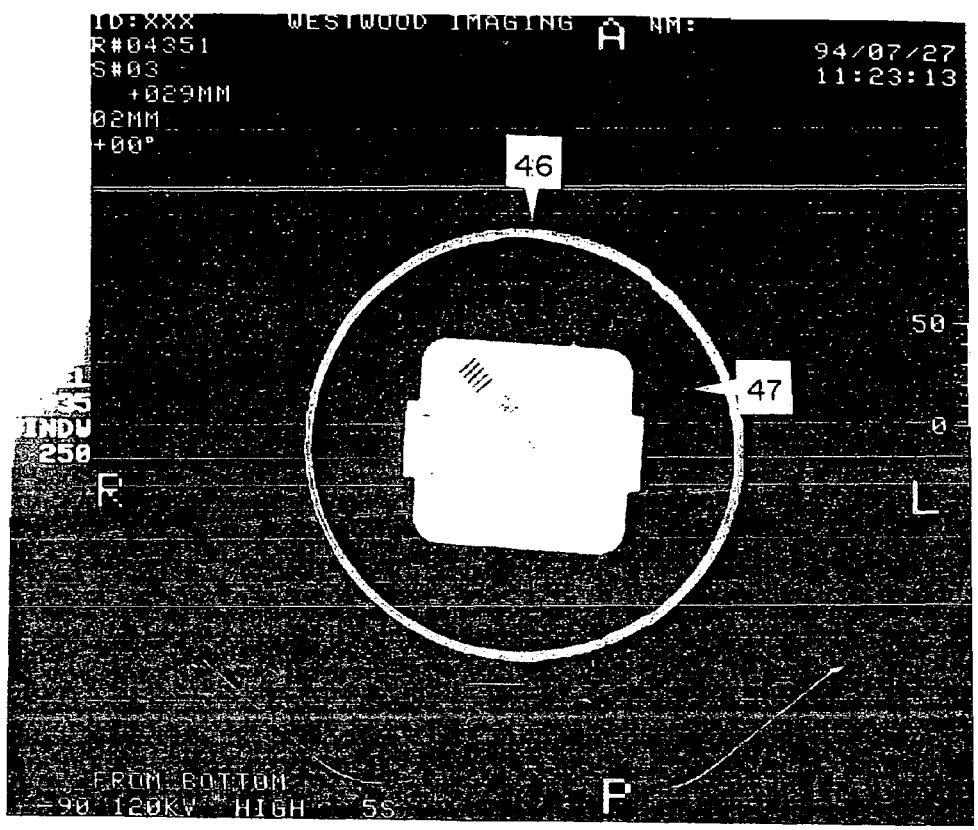
FIG. 7 is a radiograph of the marker illustrated in FIG. 6 imaged on the surface of a CT phantom.

FIG. 6 illustrates an intermediate density marker 46 useful in CT scanning applications. The marker 46 is shown imaged on the surface of a CT phantom 47 in FIG. 7. The CT phantom 47 is available from the General Electric Corporation under the designation GE #46-241-85-2GI. The marker comprises a vinyl strip 48 having a plurality of apertures 50 formed therein. When the marker is imaged together with an associated tissue structure, the apertures indicate, as illustrated in FIG. 7, whether the marker is in the axial plane and also indicates whether the CT cut is high, through the middle or low with an accuracy of plus or minus about 1 mm. In addition, the apertures provide a site for needle insertion.

The strip 48 is preferably from about 1 mm to about 4 mm thickness, from about 1 cm to about 4 cm in width and from about 5 cm to about 20 cm in length. In the illustrated embodiment, the strip 48 is about 2 mm thick, about 2 cm wide and about 8 cm long. The apertures 50 are about 1 cm in diameter and are space about 0.5 cm apart. As those skilled in the art will appreciate, the length, width and thickness of the strip may be varied as long as it is large enough to image clearly.

Markers constructed from a number of different materials and suitable for radiographing tissues representing a broad range of densities have been illustrated above. Those skilled in the art will recognize, however, that there are a great number of other marker configurations as well as other materials, either alone or in combination, which are of an intermediate density and which could just as easily be used to practice the present invention.

As noted above, the density and thickness of the marker is selected based on the density of the tissue being examined and the energy of the radiation being applied. In general markers are designed to absorb from about 2% to about 75% of the incident radiation. For example, in certain CT applications, the marker is constructed to absorb as little as from about 2% to about 5% of the incident radiation. Again, the governing parameters are that the marker must absorb enough radiation to cast a legible shadow without obscuring underlying anatomical detail.

Additional factors that influence the ultimate choice of the material from which the marker is constructed include the cost of the material, its toxicity and the ease with which the marker can be manufactured. It must also be emphasized again that the selected material must be of a uniform density so that the radiographic image of the marker has a uniform, translucent appearance without visible irregularities, conflicting striations or granulations which might obscure the resolution of anatomical detail.

The present invention further contemplates a system of partially radiolucent, partially radiopaque markers which are provided in a range of densities and thickness so that selected markers comprising the system may be used in radiographing tissue structures representing the various tissue densities enumerated above at the corresponding radiation energy range. In addition, the markers are provided in a variety of shapes to enhance the information communicated by the markers. In this regard, the markers may be shaped in accordance with a universal language, wherein each marker conveys a specific, universally accepted message. Such an enhancement of the information visibly communicated by the markers will expedite film interpretation and improve accuracy. For example, markers provided in the shape of an arrow, a triangle, the universal symbol of danger, or a standard medical cross could be provided to indicate an area of clinical concern on the film.

While preferred embodiments have been shown and described, various modifications and substitutions may be made without departing from the spirit and scope of the invention. Accordingly, it is to be understood that the present invention has been described by way of example and not by limitations.

I claim:

1. A non-toxic marker for mammographic examination of breast tissue that may anatomical detail present in the tissue, wherein a source of x-ray radiation is provided for generating radiation at a predetermined energy level suitable for imaging breast tissue, the marker is positioned on the breast tissue, and the marker and breast tissue are exposed to the x-ray radiation at the predetermined energy level to generate a radiographic image of the tissue having the shadow of the marker superimposed thereon, the marker comprising:
a first outer surface for contacting a patient's breast tissue; a second outer surface located on an opposite side of the marker relative to the first outer surface; and at least one non-toxic partially radiolucent, partially radiopaque material located therebetween, said at least one non-toxic partially radiolucednt, partially radiopaque material defining a density and thickness based on a density of breast tissue and the predetermined energy level of the radiation provided which absorbs from about 20% to about 75% of the incident radiation and, in turn, generates a radiographic image of the tissue having the shadow of the marker superimposed thereon with any anatomical detail present in the tissue clearly visible through the radiographic shadow projected by the maker.

2. A mammographic marker as defined in claim 1, wherein the non-toxic partially radiopaque, partially radiolucent material is selected from the group including: (i) rubber having a thickness of less than about 0.4 inches; (ii) plastic having a thickness of less than about 0.2 inches; (iii) vinyl having a thickness of less than about 1 mm; and (iv) aluminum having a thickness of less than about 0.022 inches.

3. A mammographic marker as defined in claim 2, wherein the non-toxic partially radiopaque, partially radiolucent material is selected from the group including: (i) rubber having a thickness within the range of 0.2 to about 0.4 inches; (ii) plastic having a thickness within the range of about 0.1 to about 0.2 inches; (iii) vinyl having a thickness within the range of about 0.75 mm about 1 mm; and (iv) aluminum having a thickness within the range of about 0.011 to about 0.022 inches.

4. A mammographic marker as defined in claim 2, wherein the plastic is impregnated with a metal.

5. A mammographic marker as defined in claim 1, wherein the non-toxic partially radiopaque, partially radiolucent material includes metal and plastic having an overall thickness of about 0.015 to about 0.04 inches.

6. A mammographic marker as defined in claim 5, wherein the non-toxic partially radiopaque, partially radiolucent material includes metal and plastic having an overall thickness of about 0.04 inches.

7. A mammographic marker as defined in claim 5, wherein the plastic is impregnated with the metal.

8. A mammographic marker as defined in claim 7, wherein the plastic is impregnated with barium.

9. A plurality of mammographic markers as defined in claim 1, including: a first marker defining the shape of a circle; a second marker defining the shape of a triangle; and a third marker defining the shape of a straight line.

10. A plurality of mammographie markers as defined in claim 9, further including; a fourth marker defining the shape of cross; and a fifth marker defining the shape of an arrow.

11. A method of mammographic examination of breast tissue that may have anatomical detail present in the tissue, comprising the steps of:
providing a source of x-ray radiation having a predetermined energy level capable of generating radiation suitable for imaging breast tissue;
providing a non-toxic partially radiolucent, partially radiopaque marker having a radiographic density and thickness which, based on the density of a breast tissue and the predetermined energy level of the radiation provided, absorbs from about 2% to about 75% of the incident radiation and permits the marker to both project a radiographic shadow and transmit sufficient radiation to image anatomical detail present in breast tissue when the marker and the tissue are exposed to the predetermined level of x-ray radiation during mammographic examination;
positioning the marker on the breast tissue; and
exposing the marker and the tissue to the x-ray radiation at the predetermined energy level, and generating a radiographic image of the tissue having the shadow of the marker superimposed thereon with any anatomical detail present in the tissue clearly visible through the radiographic shadow projected by the marker.

12. A method of mammographic examination as defined in claim 11, further compromising the steps of adhesively securing the marker to a patient's breast tissue, and transmitting radiation within the range of about 20 kV to about 40 kV through the marker and the tissue.

13. A method of mammographic examination as defined in claim 11, wherein the marker is selected from the group including: (i) a marker comprising rubber having a thickness of less than about 0.4 inches; (ii) a marker comprising plastic having a thickness of less than about 0.2 inches; (iii) a marker comprising vinyl having a thickness of less than about 1 mm; and (iv) a marker comprising aluminum having a thickness of less than about 0.022 inches.

14. A mammographic marker as defined in claim 1, wherein the non-toxic partially radiolucent, partially radiopaque material is of a uniform density such that the radiographic image of the marker has a uniform, translucent appearance without visible irregularities, conflicting striations or granulations which might obscure the resolution of underlying anatomical detail.

15. A method of mammographic examination as defined in claim 11, further comprising providing a marker having a non-toxic partially radiolucent, partially radiopaque material that is of uniform density, and generating a mammographic image of the marker having a uniform, translucent appearance without visible irregularities, conflicting striations or granulation obscuring the resolution of any underlying anatomical detail present in the tissue.

16. A non-toxic marker for radiographic examination of tissue that may have anatomical detail present in the tissue, wherein a source of x-ray radiation is provided for generating radiation at a predetermined energy level suitable for imaging tissue having a predetermined tissue density, the marker is positioned on the tissue, and the marker and tissue are exposed to the x-ray radiation at the predetermined energy level to generate a radiographic image of the tissue having the shadow of the marker superimposed thereon, the marker comprising:
- a first outer surface for contacting a patient's skin;
- a second outer surface located on an opposite side of the marker relative to the first outer surface; and
- at least one non-toxic partially radiolucent, partially radiopaque material located between the first and second outer surfaces, said at least one non-toxic partially radiolucent, partially radiopaque material defining a density and thickness based on the predetermined tissue density and the predetermined energy level of the radiation provided which absorbs from about 2% to about 75% of the incident radiation and, in turn, generates a radiographic image of the tissue having the shadow of the marker superimposed thereon with anatomical detail present in the tissue clearly visible through the radiographic shadow projected by the marker, and said at least one non-toxic partially radiolucent, partially radiopaque material is of a uniform density such that the radiographic image of the marker has a uniform, translucent appearance without visible irregularities, conflicting striations or granulations which might obscure the resolution of underlying anatomical detail.

17. A radiographic marker as defined in claim 16, wherein the non-toxic partially radiopaque, partially radiolucent material is selected from the group including: (i) rubber having a thickness of less tan about 0.4 inches; (ii) plastic having a thickness of less than about 0.2 inches; (iii) vinyl having a thickness of less than about 1 mm; and (iv) aluminum having a thickness of less than about 0.022 inches.

18. A radiographic marker as defined in claim 17, wherein the plastic is impregnated with a metal.

19. A plurality of radiographic markers as defined in claim 16, wherein each of the plurality of markers defines a respective radiographic density different than the other markers and corresponds to a respective tissue density for imaging tissue having that density, and including (i) a first marker defining a radiographic density approximately equal to the density of water for imaging relatively soft tissue; (ii) a second marker defining a radiographic density approximately equal to the density of the bones of a patient's extremities for imaging relatively intermediate density tissue; and (iii) a third marker defining a radiographic density approximately equal to the density of at least one of a skull, spine and chest of a patient for imaging relatively dense tissue.

20. A radiographic marker as defined in claim 16, wherein the marker is a mammographic marker for mammographic examination of breast tissue, the marker is adhesively attachable to a patient's breast tissue for positioning the marker on the breast tissue, and the predetermined level of the x-radiation is within the range of about 20 kV to about 40 kV.

21. A method of radiographic examination of tissue that may have anatomical detail present in the tissue, comprising the steps of:
- providing a source of x-ray radiation having a predetermined energy level capable of generating radiation suitable for imaging a predetermined tissue density;
- providing a non-toxic partially radiolucent, partially radiopaque marker having a radiographic density and thickness which permit the marker to both project a radiographic shadow and transmit sufficient radiation to image anatomical detail present in tissue having the predetermined tissue density, when the marker and the tissue are exposed to the predetermined level of x-ray radiation during radiographic examination, said providing step including providing a marker having a density and thickness based on the predetermined tissue density and the predetermined energy level of the radiation provided that absorbs from about 2% to about 75% of the incident radiation, and that includes a non-toxic partially radiolucent, partially radiopaque material of a uniform density such that the radiographic image of the marker has a uniform, translucent appearance without visible irregularities, conflicting striations or granulations which might obscure the resolution of underlying anatomical detail;
- positioning the marker on the tissue having the predetermined tissue density; and
- exposing the marker and the tissue to the x-ray radiation at the predetermined energy level, and generating a radiographic image of the tissue having the shadow of the marker superimposed thereon with any anatomical detail present in the tissue clearly visible through the radiographic shadow projected by the marker.

22. A plurality of mammnographic markers as defined in claim 9, wherein each marker includes an adhesive and is adhesively attachable to the breast tissue.

23. A plurality of mammographic markers as defined in claim 1, wherein each marker defines a shape that conveys a specific message, including a first marker defining a circular shape, a second marker defining a triangular shape, and a third marker defining a linear shape.

24. A method of mammographic examination as defined in claim 11, further comprising the steps of providing a plurality of said markers in predetermined shapes enhancing the information communicated by the markers, including: (a) a first marker defining the shape of a circle; (b) a second marker defining the shape of a triangle; and (c) a third marker defining the shape of a line.

25. A method of mammnographic examination as defined in claim 24, wherein said step of providing a plurality of said markers in predetermined shapes further includes providing: a fourth marker defining the shape of an arrow.

26. A method of mammographic examination as defined in claim 11, further comprising the steps of adhesively securing the marker to a patient's breast tissue.

* * * * *